Figure 3:
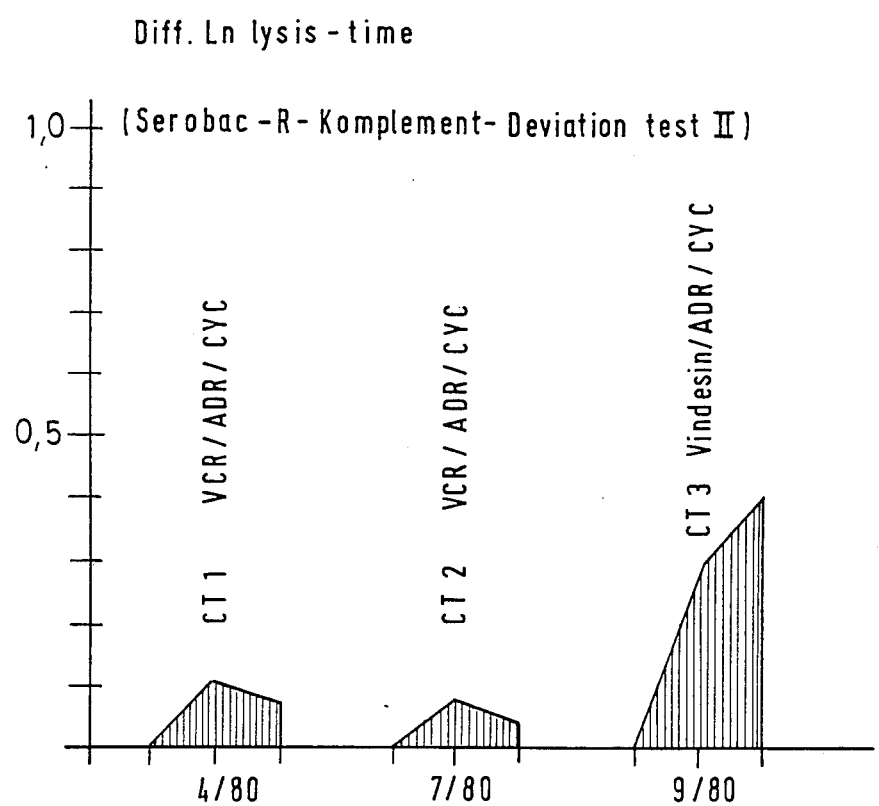

United States Patent [19]

Bartos et al.

[11] Patent Number: 4,686,194
[45] Date of Patent: Aug. 11, 1987

[54] SERIOIMMUNOLOGICAL PROCESS FOR DETERMINING THE IN-VIVO EFFECTIVENESS OF CYTOSTATIC AGENTS

[75] Inventors: Dezsö S. Bartos, Solingen, Fed. Rep. of Germany; Denis Fitzpatrick, County Cork, Ireland

[73] Assignee: Bartos Patent Development & Holding Company, Limited, Dublin, Ireland

[21] Appl. No.: 485,068

[22] Filed: Apr. 14, 1983

[30] Foreign Application Priority Data

Apr. 21, 1982 [IE] Ireland ................................. 942/82

[51] Int. Cl.$^4$ ........................................... G01N 33/536
[52] U.S. Cl. .................................... 436/536; 436/507; 436/513; 436/516; 436/521; 436/63
[58] Field of Search ............... 436/507, 513, 516, 521, 436/536, 64; 424/2, 9

[56] References Cited

U.S. PATENT DOCUMENTS 4,132,769  1/1979  Osther ................................. 436/516
4,143,124  3/1979  Masson et al. ....................... 436/513
4,174,385  11/1979  Reid .................................... 436/536

FOREIGN PATENT DOCUMENTS 2729893  5/1977  Fed. Rep. of Germany .......... 424/9

OTHER PUBLICATIONS

Persellin, et al., Clin. Exp. Immunol., vol. 46, (1981), pp. 350–354.
Müller, et al., Eur. J. Cancer Clin. Oncol., vol. 18, No. 4, (1982), pp. 327–332.
Schwenk, et al., Klin. Pädiat., vol. 190, (1978), pp. 453–459.
Stimson et al., J. Clin. Path., vol. 28, (1975), pp. 868–871.
Thomson et al., Acta. haemat., vol. 66, (1981), pp. 210–213.
Norgaard-Pedersen, et al., Immunoelectrophoretical Quantitation of Human Placental Lactogen Hormone (HPL).

Primary Examiner—Christine M. Nucker
Assistant Examiner—Stephen C. Wieder
Attorney, Agent, or Firm—Wegner & Bertschneider

[57] ABSTRACT

The in-vivo effectiveness of cytostatic agents against immunological active tumors is determined by measuring immune markers and/or immune parameters in the serum before and up to 3 days after the application of the cytostatic agent. Preferably the deviation of coomplement binding capacity is used as immune parameter.

8 Claims, 6 Drawing Figures

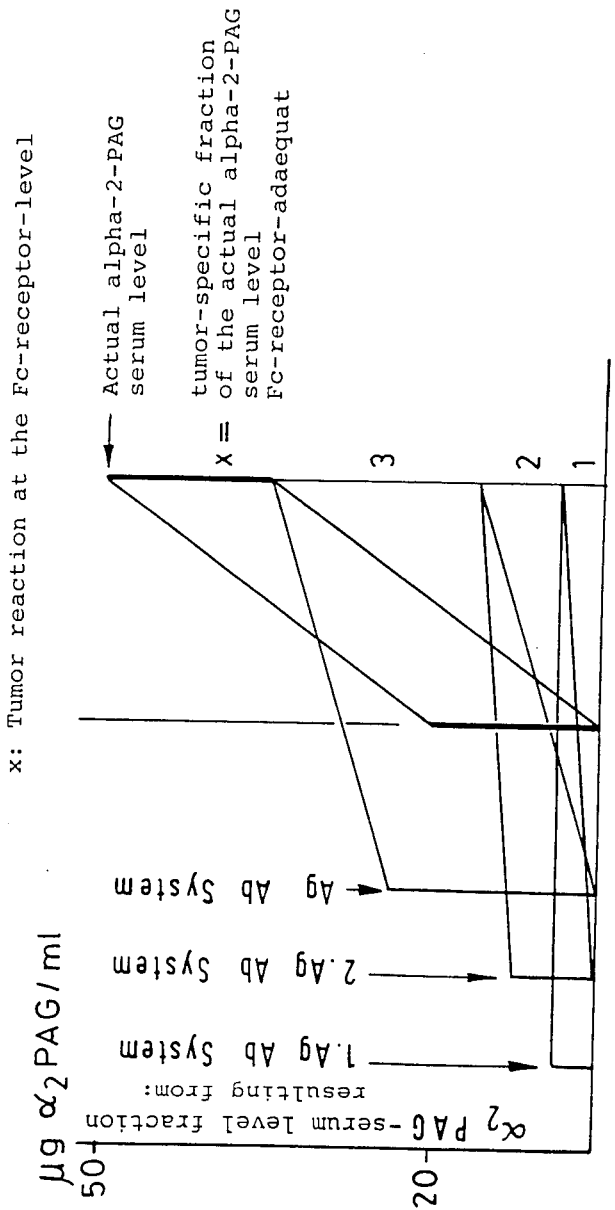
Definition of the tumor-specific fraction of the actual alpha-2-PAG serum level (explanation see text)

Reaction forms of the alpha-2-PAG immune response

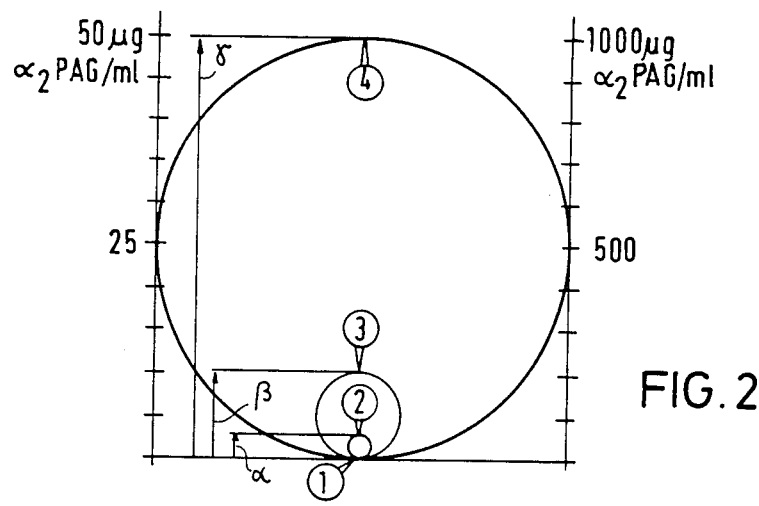

FIG. 2

A. Tumorspecific alpha-2-PAG serum fraction in advanced tumors (however not with cachexy or in a state of energy)

①  under 1.0 microgram/ml alpha-2-PAG = immune active tumour humoral

②  up to 2.5 microgram/ml alpha-2-PAG = immune answer negative tumour humoral

③  up to 20/25 microgram/ml alpha-2-PAG = immune answer positive tumour humoral

④  over 30 microgram/ml up to ca. 300/500 microgram/ml alpha-2-PAG = immune reactive tumour B. Schematic demonstration of the three levels of alpha-2-PAG immune response $\alpha$) supressor T-cell-level and macrophage function
$\beta$) Fc-receptor level (humoral and cellular)
$\gamma$) C-3 receptor level Alpha-2-PAG short-time analysis after chemotherapy (=CT1 24 and 48 hours after administration of medication in mammacarcinoma patient with the CEA-progression course in figures 4 and 5).

SERIOIMMUNOLOGICAL PROCESS FOR DETERMINING THE IN-VIVO EFFECTIVENESS OF CYTOSTATIC AGENTS

The invention relates to a seroimmunological process for determining the in vivo effectiveness of cytostatic agents.

In the last 20 years cytostatic agents (cancer inhibiting medication) have resulted in a significant advance in the therapy of malignant growths.

Initially, individual substances were used. However, these only resulted in, depending upon the medication and type of tumor, at most a positive effect in 35% of cases. This monotherapy was replaced in the 70's by combination therapy. A number of cytostatic agents, normally 2 to 4, are administered together in combination. The therapeutic results have significantly improved.

Further increases in the number of cytostatic agents administered in combination therapy did not, however, lead to further advances. A therapeutic plateau was reached. This is understandable, since normally even when more cytostatic agents are administered in combination, the effectiveness/non-effectiveness of the individual substances is only slightly altered. The improved therapeutic results were achieved at a cost of the toxicity and non-effectiveness of individual substances in the combination therapy. From a certain toxicity level the advantages and the disadvantages cancel each other out.

There is, therefore, an urgent necessity to administer cytostatic agent in targeted manner or under controlled conditions.

By controlled conditions is meant the previous testing of the effectiveness/non-effectiveness of the individual cancer medications in a suitable in-vitro test system. In recent years an increasing number of publications on this theme have appeared, for example:

H. Limburg. A. K.—J-Brachetti:"16jährige klinische Ergebnisse in der Behandlung des Ovarialkarzinoms nach dem Chemotherapic-Resistenztest", Geburtshilfe und Frauenheilkunde 41 (1981), pages 126–135.

M. Volm et al: "Sensibilitätstestung menschlicher Tumoren gegenüber Zytostatika mit einem in-vitro Kurzzeittest (Kooperative Studie für Sensibilitätstestung von Tumoren (KSST) des Bundesministeriums für Forschung und Technologie der Bundesrepublik Deutschland", Deutsche Medizinische Wochenschrift 105 (1980), pages 1493–1496.

M. Kaufmann et al: "Chemosensibilitätstestung des Ovarial- und Mammakarzinoms - Möglichkeiten und Grenzen verschiedener Methoden und ihre klinische Anwendung", Geburtshilfe und Fraucnheilkunde 42 (1982), pages 161–165.

S. E. Salmon et al: "New Drugs in Ovarian Cancer and Malignant Melanoma: In vitro Phase II Screening with the Human Tumor Stamm Cell Assay", Cancer Treatment Reports, Volume 65, No. 1–2, January/February 1981 1–12.

By the controlled use of cytostatic agents is meant a procedure whereby the effectiveness/non-effectiveness of therapy is followed by means of tumor-marker measurement (monitoring the tumor). This theme was discussed in detail at the Symposium in Cologne in November 1980. G. Uhlenbruck and G. Wintzer: "Carcinoembryonales Antigen und andere Tumormarker". Ein Symposiumsband; Tumor-Diagnostik Verlag D-7250 Leonberg. For the in-vitro cytostatic sensitivity test one requires living isolated tumor cells obtained at an operation. This procedure requires the presence of a special laboratory and the assistance of specialists on the spot.

One can follow the progress of the tumor from the beginning of one therapy cycle to the beginning of another therapy cycle and the effectiveness or non-effectiveness of the therapy can be determined but only in a small number of cases is it possible to make a prediction or to assign the effectiveness to the individual components of the cytostatic combination. The reaction of the tumor-marker is, with a few exceptions, for example the $\beta$-HCG-concentration-change in short-time analysis in choriocarcinoma, too slow to make such a prediction possible.

Were it possible to administer cytostatic agents in a targeted manner then there would improved therapeutic results with lower levels of cytostatica. This would itself be a significant advance.

According to the latest discoveries the humoral immunoreaction in tumor cases is assuming an increasingly important role. Depending on the type of cancer in up to 70% of tumor cases either circulating immunocomplexes or free humoral antibodies against the cell membrane structure of tumor cells can be determined. The circulating immunocomplexes come from cell fragments of dead cells or by secretion of antigens by the tumor cells. This immune happening can be detected by various laboratory methods.

Free humoral antibodies can be detected by the indirect immunofluorescence method in living isolated autologous tumor cells (D. Stefan Bartos: Communication to the third working party on tumor immunology in gynaecology, March 1982 in Bonn—publication in preparation).

Circulating immunocomplexes can be detected in cancer cases by various methods, for example the c-q-J125-binding test, PEG-precipitation method (PEG: polyethylene glycol).

Raji-cell-technique original or the J-125-labelled protein-A-technique. By a complement deviation test or by measuring the total complement serumactivity one can also measure the circulating immunocomplexes or the resultant secondary alternations in the composition of the serum samples.

The new procedure is based on a seroimmunological method that consists of two steps. These are:

1. The recognition that the alpha-2-PAG (pregnancy-associated-alpha-2-glycoprotein) or as synonym SP-3 (placenta-specific protein 3) is not a tumor-marker, as has been described, but is an immunomarker which behaves as a very sensitive tumor-marker.

2. That the short-time analysis of immunomarker is used to detect the effectiveness or non-effectiveness of cytostatic agents, whereby one analysis preferably the same immunomarker also in the long term from the beginning of a therapy cycle to the beginning of another therapy cycle, additionally, and for this purpose, one preferably administers the individual components of the cytostatic combination sequentially when deciding upon therapy so that the effectiveness/non-effectiveness of the individual medications can be determined.

The state of knowledge of alpha-2-PAG goes back to the work of H. Bohn and W. Bauer which was published in the year 1979. H. Bohn und H. W. Bauer: "Schwangerschaftsassoziiertes Alpha-2-Glykoprotein (Alpha-2-PAG): Bedeutung seiner Bestimmung bei malignen Erkrankungen", Laboratoriumsblätter 29, pages 119–126 (1979).

D. Stefan Bartos has proved that alpha-2-PAG is not a tumor-associated protein but an immunomarker.

D. Stefan Bartos: Der intra-individuelle Alpha-2-PAG (schwangerschaftsassoziiertes Alpha-Glykoprotein) -Blutserumspiegel als 'Tumormarker' beim Mammakarzinom. Ergebnisse des Solinger Mammatumoren-Scrumpanels 1978–1980. Page 357 in H. Uhlenbruck und G. Wintzer: CEA and andere Tumormarker: Ein Symposiumsband/Tumor-Diagnostik Verlag D-7250 Leonberg, 1981, gives the results of a prospective study in the years 1978 to 1980 all mammatumor cases in the St. Lukas-Klinik, Solingen-Ohlings, (445 cases), of which 38 were metastasing mammacarcinoma carcinoma cases were seroimmunologically collected. Preoperative/ pretherapeutic serum samples were collected as well as those from patients with ongoing treatment at the time therapeutic measures were taken daily and subdivided and stored at −28° C. The main point of the study was the determination of the clinical value of a continual intraindividual alpha-2-PAG-level. On the basis of the results and on other knowledge concerning the function of alpha-2-PAG a model of (alpha-2-PAG) immune response in tumor cases was developed. Mammacarcinoma can be divided into three types on the basis of their immune response: 1. immunoreactive, 2. alpha-2-PAG immune response positive, 3. alpha-2-PAG immune response negative. Alpha-2-PAG is not a tumor-marker. It is an indicator of the secondary immune response of tumor break down or increase in tumor mass. In the case of immune reactive mammacarcinoma the intraindividual alpha-2-PAG-level has the function of a highly sensitive "tumor-marker". The comparative studies with the alpha-2-PAG-level in pregnancy and in tumor patients with accompanying virus infection allow the inauguration of the term "immunoreactive mammacarcinoma". In immunoreactive mammacarcinoma the variation in the intraindividual level of alpha-2-PAG in serum is manifold of that to be registered in virus-infection. The strength of the immune reaction approximates that of pregnancy. Further knowledge raises the suspicion, that in immune-reactive mammacarcinoma a reaction of the body with a virus-genom-coded tumor-associated membrane-bound transplantation antigen occurs. This immunoreactivity is of prognostic importance.

D. Stelan Bartos: Brweiterte praediktive Tests zur Chemo-und Hormontherapie sowie zur Nachsorgeplanung beim Mammakarzinom, pages 11–26, im 2. Arbeitsgespräch Tumorimmunologie in der Gynäkologie Lübeck, den 16.–18.1.1981. Herausgeber D. Krebs discloses the immune marker function of alpha-2-PAG in mammacarcinoma.

Stimulated by the publication of Stimmson et al we have since 1977 involved ourselves extensively with the possible tumor-marker function of the pregnancy-associated alpha-2-glycoprotein in mammacarcinoma and ovarial carcinomia. In ovarial carcinoma the alpha-2-PAG reaction forms post-operative or in remission as a result of effective therapy or in the case of a progression with few exceptions is always uniform and progresses in the range of tumor-specific alpha-2-PAG serum level fraction of 5 to 25 microgram per milliliter. In contrast, in mammacarcinoma the picture is heterogeneous. Our results have been published for the first time in November 1980 at the CEA-Symposium in Cologne. Further discoveries were communicated to the AIO-Symposium in December 1980 in Göttingen.

The function of the tumor-specific fraction of the actual intraindividual alpha-2 serum level can be seen in FIG. 1.

The alpha-2-PAG is product of the lymphatic system. Its half-life is ca. 6 days. Alpha-2-PAG is produced by exogenous or endogenous antigen persistence and is particularly connected with the partial locofocal immune tolerance. From the individual antigen/antibody balance or the strength of the cellular immune defense each anti-Ag/Ab-system results for each Ag/Ab-system—antigen-specific— a locofocal alpha-2-PAG sysnthesis and as a result of this a partial fraction of the general alpha-2-PAG serum level. The actual alpha-2-PAG serum level is therefore a summation product of all exogenous and endogenous antigens at a particular time and varies considerably from individual to individual.

There exist three levels (reaction forms) of alpha-2-PAG immune response with increasing strength of reaction:

a. supressor-T-cell-level and level of the macrophage
  b. Fc-receptor level (humoral and antibody directed cellular)
  c. receptor level (humoral and c-1-inactivator or c-3-receptor-determined in the framework of the antibody directed fraction of the cellular immune reaction).

The strength of the alpha-2-PAG immune response (=tumor-specific fraction of the actual alpha-2-PAG blood serum) is measured:

a. by the antigens of the tumor cells
  b. from the tumor mass
  c. from the method of spread of the tumor and its anatomical relationship to the lymphatic system
  d. from the strength of the immune response (general condition, age genetic factors, etc.).

The tumor-specific fraction of the actual intraindividual alpha-2 serum level is an expression of the locofocal and regional or the general immune tolerance against the tumor tissue. This is simultaneously an expression of the possible strength of the immunological defence reaction and of the highest prognostic importance. The observed reaction forms of the alpha-2-PAG response in mammacarcinoma are summarized in FIG. 2. The perioperative analysis of serum samples from 143 primary treated mammacarcinomas indicates that 36% of the mammacarcinomas are immune-active, a further 42% are alpha-2-PAG-response positive and the remaining 22% are alpha-2-PAG-immune-response negative.

FIG. 2: Reaction form of the alpha-2-PAG immune response in tumor.

In humoral alpha-2-PAG immune reactive tumor forms one finds almost exclusively humoral antibodies of the type IG-G and/or the type IG-M against the structure of the tumor cell. The strength of alpha-2-PAG immune response is of the highest prognostic importance in mammacarcinoma. Our clinical material can only be worked up stepwise. Already the results in FIG. 3 make clear the importance of this discovery. The beginning of lymphnode metastasis as well as the diameter of the primary tumor is significantly dependent on the strength of the alpha-2-PAG immune response. The number of LK-positive mammacarcinomas 53/101 at the time of primary therapy were staged according to the size of the primary tumor diameter and, depending on the strength of the alpha-2-PAG immune response, determined as perioperative alpha-2-PAG serum level decrease. This grading occured at a tumor-specific alpha-2-PAG serum level fraction of 10 microgram/ml. If an alpha-2-PAG immune response is greater than 10 microgram/ml the lymphnodes are attacked in 6/43 (=13,6%), 11/20 (=55%), and 10/15 (=67%) of the cases compared with 9/30 (=30%), 7/9 (=78%), and 10/10 (=100%) with an increase of the alpha-2-PAG immune response to the tumor of less than 10 microgram/ml.

The tumor-specific fraction of the actual alpha-2-PAG serum level exercises the function of a high-sensitive tumor-marker which will be of greater importance in the future in the diagnostic-therapeutic decision.

The detectability of circulating immune complexes and of free humoral antibodies against tumor cell membrane antigens in mammacarcinoma is dependent on the alpha-2-PAG reaction strength. In the meantime this statement could also be proven with isolated monocell mammacarcinoma cell suspension by means of Laser-immuno-fluorescence method. The detectability of free humoral antibodies, mainly IgA and IgM, as also occasional immunoglobulin-G-antibodies, against the membrane structure of isolated and cultivated autologous tumor cells is dependent on the alpha-2-PAG reaction strength. With this a direct proof for the immune marker function of alpha-2-PAG has been obtained.

The work of D. Stefan Bartos has further shown that in tumor cases where the tumor-specific alpha-2-PAG fraction in serum is higher than 20 to 30 micrograms per milliliter serum, free humoral antibodies of type IG-G and IG-M can be determined and these tumor cases have a significantly higher favorable prognosis in mammacarcinoma (Vortrag am 3. Arbeitsgespräch Tumorimmunologie in der Gynäkologie in March 1982 in Bonn. Publication in preparation).

This knowledge is of the utmost importance for the newly discovered procedure.

According to the invention there is provided a serial immunological process for determining the effectiveness of cytostatic agents on immunologically active tumors, wherein by administration of the agents, either alone or in combination, and short-time scale analysis of an immuno-marker/immune parameter or combined estimation of these parameters, a prediction is made either, on the basis of a destruction of tumor and a temporary displacement of the tumor antigen immune defense balance, of an effective medication, or on the basis of the absence of such charges or a measurable inhibition of production/decrease in concentration of the parameters studied of an ineffective medication.

Object of this invention is a process for the determination of the in-vivo effectiveness of cytostatic agents against immunological active tumors, characterized in that immune markers and/or immune parameters are measured in the serum before and up to 3 days after the application of the cytostatic agent.

In one embodiment of the invention the parameter studied is the tumor-specific portion of the individual alpha-2 serum PAG.

In one aspect the invention provides a serial immunological process for early detection of effectivity or non-effectivity of cytostatic agents (cancer inhibiting substances) on immunologically active tumors, wherein after administration of the agent in question or a combination of agents by short-time analysis of an immuno-marker/immune parameter or combined estimation of these parameters a prediction can be made, that in the case of effective medication a destruction of tumor and a temporary displacement of the tumor antigen immune defence balance and a short-time displacement of the parameter studies occurs or in the case of non-effective medication either the absence of these changes or a measurable inhibition of production/decrease in concentration of the parameters being studied occurs because of the inhibiting effect of the cytostatic agent on the function of the body's own competent cells.

Preferably, by suitable studies or by prior analysis of the parameter to be studied, at a suitable point in the case of the individual patient, the quality of the immune response and the immune capacity for the tumor is determined and these data are allowed for in the interpretation of the results of the process so that a more valid prediction can be made.

Usually, in the case of the parameter to be studied the tumor-specific portion of the individual alpha-2-PAG serum level is studied.

Alternatively, in the case of the parameter being studied the total anti-complement activity of the serum sample is measured under standard conditions.

Typically, in the case of the parameter being studied the changes in concentration or change in quality of circulating immunocomplexes are studied which are then related to the progression of the tumor.

1. In immunologically active tumors an equilibrium exists between the immunocapacity (the immunological defence possibility of the organ attacked by the tumor) and the amount of antigen present (the tumor-mass in the organism with foreign antigenicity for the individual, which is recognized and which provokes an immunological reaction). This equilibrium can be described by the equation amount of tumor antigen=immunocapacity.

2. If one administers a cytostatic agent and this is strongly effective, then this results in the death of tumor-cells, and a decrease in the amount of tumor. Combined with this, tumor antigens are released. The equilibrium described above is displaced for a short time in the direction of increased antigen excess. The immune system reacts in a highly sensitive and transient manner to the displacement of this equilibrium. The following occur in short time:

(a) an increase in the amount of circulating immunocomplexes in peripheral various blood.

(b) Due to the saturation of free humoral antibodies a decrease occurs in the amount of free humoral antibodies.

(c) A quantitative and also a qualitative alteration occurs in the anticomplement properties of the circulating antibodies. These changes can be measured as short-term changes in the total anticomplement activity of the patient serum in a suitable analytical system as for example in the photometric Complement Fixation Test.

(d) A temporary increase of the acute phase proteins in serum occurs as a secondary reaction as a result of the destruction of tumor tissue. This increase of acute phase proteins can best be measured by means of the total anticomplement activity of serum sample.

(e) A temporary increase in alpha-2-PAG serum level increase occurs. Alpha-2-PAG is an immuno-marker and the lymphatic system reacts promptly and temporarily to the displacement of the antigen-antibody balance in the organism by synthesizing new alpha-2-PAG. The temporary increase in serum alpha-2-PAG is all the greater the more effective is the cytostatic agent for a given tumor level with a definitive antigenicity and a given immuno-response capacity if free humoral antibodies of IG-G and/or IG-M are present against the antigen structure of the tumor cells of the patient and if these antibodies possess the c-1q or c-3 receptor-binding capacity quality (complement-active humoral antibodies). Immunoglobulin-A antibodies are less effective.

3. If the administered cytostatic agent is not effective, tumor breakdown does not occur, the balance between the amount of anitgen (determined by tumor) and the immune defence remains more or less the same. The following do not occur:

(a) the amount of circulating immunocomplexes does not increase.

(b) The biological properties of the circulating immunocomplexes remain unchanged, the anticomplement property of the circulating immunocomplexes and of the serum sample remain identical.

(c) The increase in acute phase protein does not occur.

(d) And particularly interesting a temporary decrease of the alpha-2-PAG blood level occurs. This is explained by the fact that the cytostatic agent inhibits alpha-2-PAG-synthesis in the peripheral lymphatic system. The lymphocytes are inhibited by the cytostatic agent or are inhibited in their function by the cystatica. Alpha-2-PAG has a half-life of about six days. For example, administration of 50 mg adriblastin (=30 mg/m$^2$ body surface area) to a patient with 1.7 m$^2$ average body surface area causes a complete inhibition of alpha-2-PAG-production for approximately 24 hours. If this cytostatic agent is completely ineffective, then a resultant drop of approximately 15% in the serum alpha-2-PAG occurs. If this is strongly effective on the other hand, not only is this negative effect cancelled out but also compensated against. An increase in alpha-2-PAG occurs particularly then when the tumor is immunologically very active.

For that reason the short-time analysis of serum alpha-2-PAG is particularly suited for a seroimmunological in-vivo cytostatic sensibility test. Because in the case of alpha-2-PAG the measurement signals between the strongly effective/ineffective reaction differs so greatly, related to the reproductibility and in consideration of the case of execution of the method of analysis.

4. If a cytostatic agent is less effective, then the changes described above are less extensive.

5. It is preferable to administer the individual cytostatic components stepwise when beginning a new therapy, i.e. every 36 to 48 hours and the alpha-2-PAG serum level should be analysed every 8 to 12 hours. This makes it possible to make the most optimal predictions. A similar procedure is recommended when one uses other immune parameters mentioned above for this purpose.

Naturally, the predictive quality of the procedure described above is greater which means that the quality of the immune response is better known and the immune capacity of the individual patient against his or her tumor can be described more accurately.

For this reason it is desirable that the immune parameters which are used for the above described procedure are determined repeatly or at certain timed intervals so that pre- and postoperative and also during retreatment the levels of those immune parameters can be related to the tumor growth (for example estimation of the tumor-specific fraction of the intraindividual alpha-2-PAG blood serum level by a pre- and postoperative analysis or by analysis of this value in the tumor-free state during treatment or in the full remission state compared with the regression stage or a new progression). These estimations are preferably combined with other studies, for example, bone scintigram, X-ray studies etc., in order to make a more exact prediction.

It is obvious that, for example, in the case of a positive immunocomplex result, other chemical parameters or conditions must be allowed for, for example, if the patient suffers a virus infection, for example, varicell infection or a heavy flu, the results cannot be assigned to the tumor.

On the other hand, in the short-time analysis these unspecific effects are understandably not relevant as the unspecific effects have a slower reaction kinetic or influence on the parameters being studied.

The alpha-2-PAG estimation can also predict the strength of the response of the reaction based on the detection of free humoral antibodies and on the quality of these humoral antibodies as the alpha-2-PAG has a direct immune-marker function.

EXAMPLES

1. The estimation of alpha-2-PAG serum levels is carried out routinely by the well-known method of electroimmunodiffusion according to Laurell (rocket-immuno-electrophoresis).

The method of detection has a lower limit of 3.8 to 6 microgram alpha-2-PAG per milliliter proband serum whereby an optimal value can be determined as about 10 microgram/ml alpha-2-PAG.

For this reason a technique, the technique of limited substance method, is also preferably used. In this method all standard dilutions and all serum samples have added 1/10th by volume of an alpha-2-PAG standard solution with an alpha-2-PAG concentration of 110 microgram/ml. This guarantees that all samples and all standards contain 1/11th=10 microgram alpha-2-PAG/ml. If the alpha-2-PAG concentration in the sample is 2 microgram/ml then the value obtained is 12 microgram alpha-2-PAG/ml. The concentration differences 10 microgram (=blank value) and 12 microgram in the sample can be measured exactly. This improves the analysis method considerably and covers the clinical measurement range completely. This range lies between 1 to 2 microgram alpha-2-PAG/ml up to 250–500 microgram/ml.

It is known that in the electroimmunodiffusion method of Laurell the reproducibility from day to day is not good. On the other hand, the precision on a series of studies (intraassay reproducibility is very good, having a coefficient of variation less than ±3.5%.

For this reason previous serum samples are stored frozen under −21° C. in small amounts so that in each new study the most recent sample can also be determined again. This allows a long term control.

2. The estimation of circulating immunocomplexes can be carried out by two standard methods (a) in accordance with the work of Hoffken, H. et al: Immune complexes and prognosis of human breast cancer. Lancet, 1: 672–673, 1978, and (b) U. Koldovsky and D. Stefan Bartos: Nachweis von zirkulierenden Immunkomplexen in der Langzeitanalyse beim Mammakarzinoma mit Hilfe der Raji-Zell-J-125-Protein-A-Technik: Publication in preparation. Presented in short form at the Cancer Congress in Lausanne in October 1981.

3. Photometric reagent for the estimation of total anticomplement activity of serum samples as immune parameter. For further information see the Irish Patent Application of Bartos Patent Development and Holding Company Limited filed in April 1982 and relating to the optimized visual and photometric Complement Fixation Test (Ir. 943/82 Bartos I).

Treatment of tumor patient samples: Serum samples are contrifuged within 1 to 2 hours after a natural coagulation and the serum is stored at −21° C. On the day of the study all serum samples for a series of tests according to this procedure are analysed in one series, the serum samples are thawed out and complement activity is removed for 30 minutes at 56° C. The amboceptor-like activity of the serum samples is removed with stabilized sheep erythrocytes (a product of the firm Serobac-Ireland-Ltd. and the firm Serobac-Serobakteriologische Präparate und Immundiagnostik GmbH, D-5650 Solingen). To 800 microliter of sample after complement removal 200 microliter of stabilized sheep erythrocyte suspension 50% is added, the sample is allowed to stand for 10 minutes at room temperature and is centrifuged. The supernatant is used as a treated serum sample in the test.

Procedure: 300 microliter of pretreated serum sample is added to 300 microliter of reactant (serobac-complement deviation test II) and incubated for 180 minutes at 37° C. Then 500 microliters of a mixture are placed in a cuvette, are thermostated in an automatic cell changer, manufactured by Eppendorf, at 37° C., and the complement activity titration is begun by adding 50 microliter sheep crythrocyte suspension to yield an extinction value of 0.4. The determination of the actual complement activity of the individual samples is achieved by means of the CH-50%-lysis-time analysis. The lysis-time in seconds is transformed into natural logarithmic values and these values are used in the calculation of results.

In each series a control of blank (Bo) samples is also run always in a duplicate analysis as are all serum samples. The blank contains CFT-buffer instead of serum sample and serves as control for the spontaneous inactivation of the reaction mixture.

In addition a standard human control serum (free from circulating immunocomplexes) based on human umbilical cord serum is also run.

Evaluation of the test: The CH-50%-lysis-time of the individual blank in seconds is expressed in natural logarithms, similarly the individual value of the serum samples: The latter is then substracted from the former: This procedure gives a delta minus value which reflects an absolute value of complement consumption. These data are displayed graphically against the time of administration of the medicine. The area under this graphic display corresponds to the effectiveness of the medification and is a product of the amount of tumor and the available immunocapacity against the tumor. As these do not change much over a short period, the area is practically identical with the effectivity of the cytostatic agent.

EXAMPLE:

CH-50%-lysis-time of the blank 5 minutes 30 seconds = 330 seconds the natural logarithmic value is 5.8 similar value of the serum sample at time 0 of medical application 11 minutes 12 seconds = 672 seconds natural logarithmic value 6.51 gives a delta minus 0.71.

Delta −0.71 is a highly pathological value, the standard control serum indicates a value of delta −0.21. This means that the serum sample is highly suspect of having circulating immune complexes in high concentration.

Similar values after 24 and 40 hours following administration of medication: 24 hours delta −0.96 and after 48 hours delta −0.86. With this the increase of anticomplement activity of the serum sample after administration of medicine has an absolute value of delta −0.25 or delta 0.15 natural log. value respectively which indicates a strong increase in the amount of circulating immune complexes and suggests a strong effect of the administered medication.

The serobac-complement-deviation-test contains a ready-to-use reagent mixture consisting of amboceptor/complement and in statu nascendi resultant limiting immunocomplexes which presensibilize the complement system to the border of C-1-inactivation system. The reagent mixture and the photometric evaluation allows the detection of 2 to 5 nanogram antigen/ml reagent mixture upwards. The reproducibility of the above technique in duplicate assays was ± natural log. 0.03 absolute value in the series.

FIG. 1

Model of the tumor-specific fraction of actual intra individual alpha-2-PAG serum level.

A certain fraction of the alpha-2-PAG total serum level results from antigen persistence in the organism from each antigen-antibody immune response system. Usually, alpha-2-PAG is produced locofocally up to the time of removal of the foreign antigen in the peripheral lymphocytem in the local-regional lyphatic system. The same occurs in the case of an immunologically active tumor. The tumor also produces a certain fraction on actual intraindividual serum level. Only this tumor-specific fraction of alpha-2-PAG serum level can be used as an immune marker for the tumor.

FIG. 2

Reaction form of the alpha-2-PAG immune response

In humoral alpha-2-PAG immune-reactive tumor forms one finds almost exclusively humoral antibodies of the type IG-G and/or the type IG-M against structures of the tumor cells.

FIG. 3

Result of the effectiveness/non-effectiveness test of cytostatic agents' combination in patients with metastasing mammacarcinoma in the abdominal area.

Analysis of circulating immune complexes and acute phase protein as total anticomplement activity of the serum protein in serobac-complement deviation test II, as described above.

Analysis points of serum samples at hour 0, 24 hours and 48 hours after administration of combined medication. In April 1980 and in July 1980 application of 2 milligram vincristin i.v. 50 mg adriblastin i.v. and 600 mg cyclophosphamide i.v. as a bolus-injection at hour 0. In 4/80 clinical partial remission with this therapy which had begun 3 months previously. From 4/80 to 7/80 beginning clinical progression. In 9/1980 vincristin was replaced in the combined medication with 5 mg vindesine.

Vindesine (=eldsine) is a half-synthetic vinca-alcaloid. Clinical dissolution of a hand-size tumor in the left upper abdomen, the tumor destruction was accompanied by shaking and an increase in temperature. From this point on, a clinical renewed continuing partial remission occured. From the areas indicated on the basis of the analysis results of this immune parameter the decreasing effectiveness of the first chemotherapeutic combination is visible. The exchange of the vinca-alcaloid vincristin for vindesine 5 mg i.v. brought a renewed high-level effectiveness of the chemotherapy.

The tumor was immunologically very active. 10 months later, as part of a laparatomy, autologous tumor cells were obtained and kept in tissue culture for weeks. As well as circulating immune complexes free humoral antibodies of type IG-G and IG-M could be demonstrated repeatly.

The reaction picture of alpha-2-PAG analysis at the same time gave similar alterations in serum levels, however, each time a short rise, whereby the largest rise was recorded at the point 9/1980. At CT 1+13%, at CT 2+7%, and at CT 3+18% 24 hours after the 0-hour of medication application.

Figure 4:
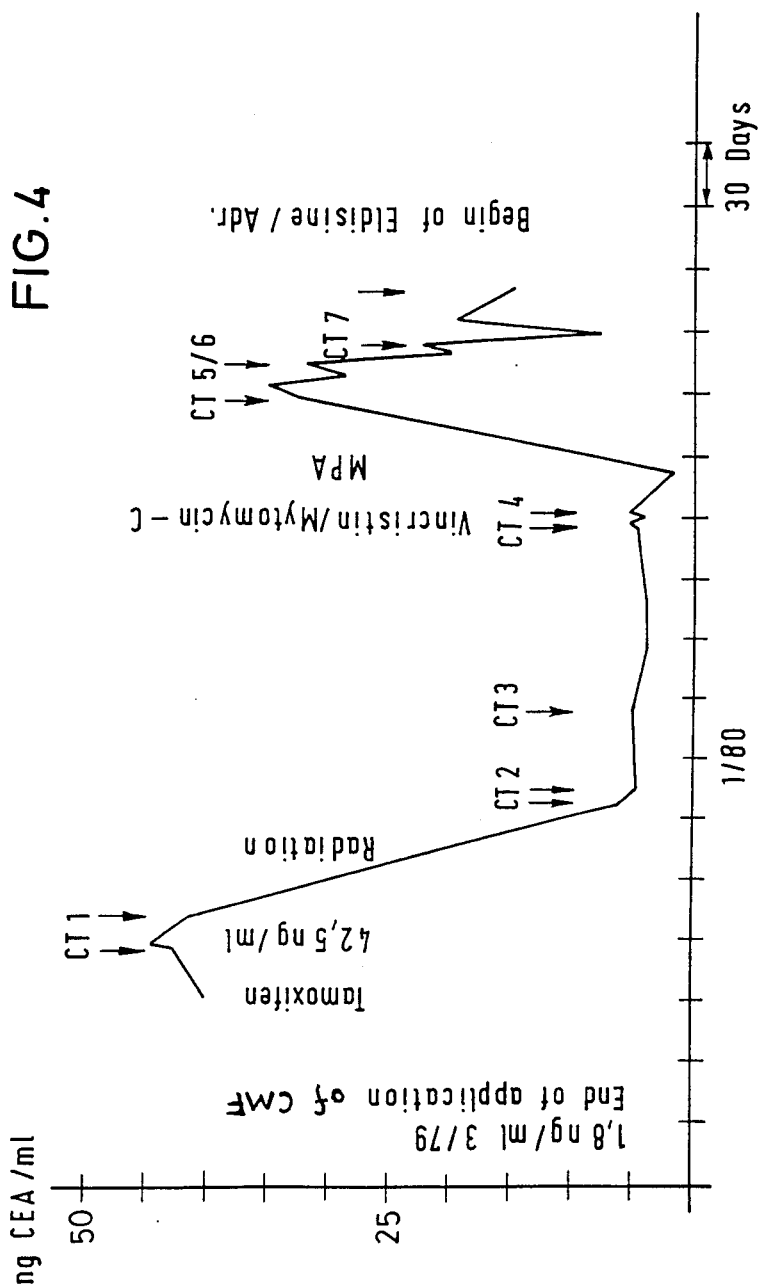
Figure 5:
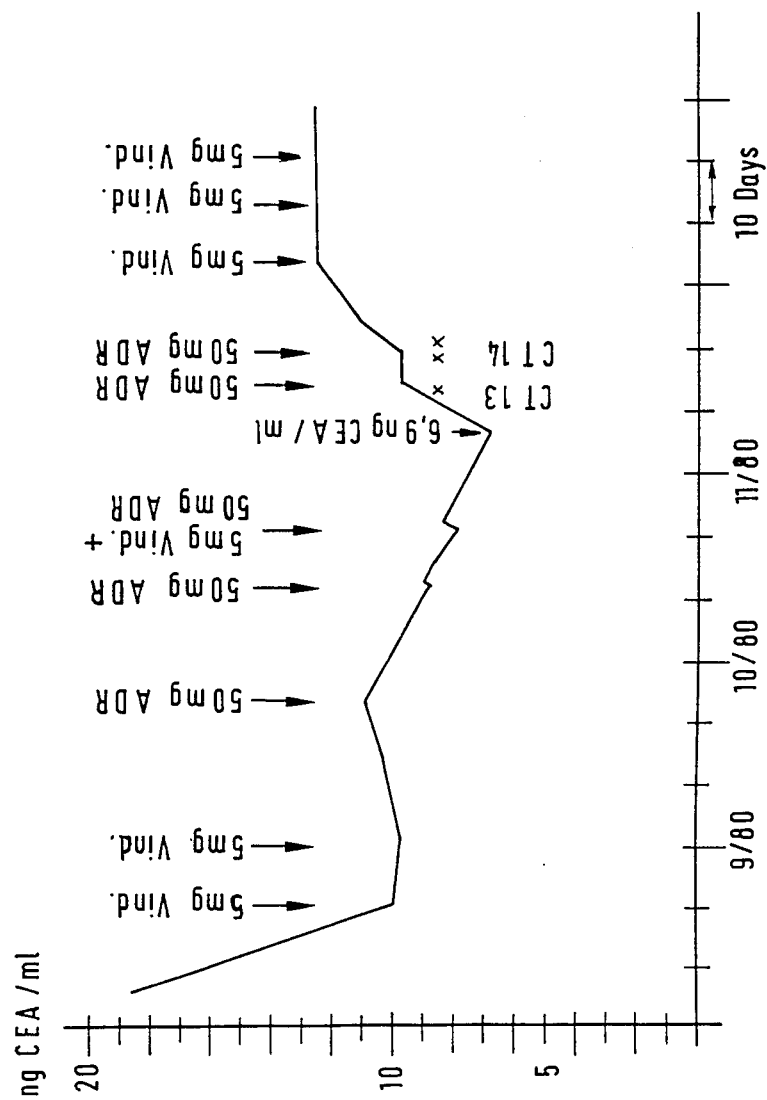
Figure 6:
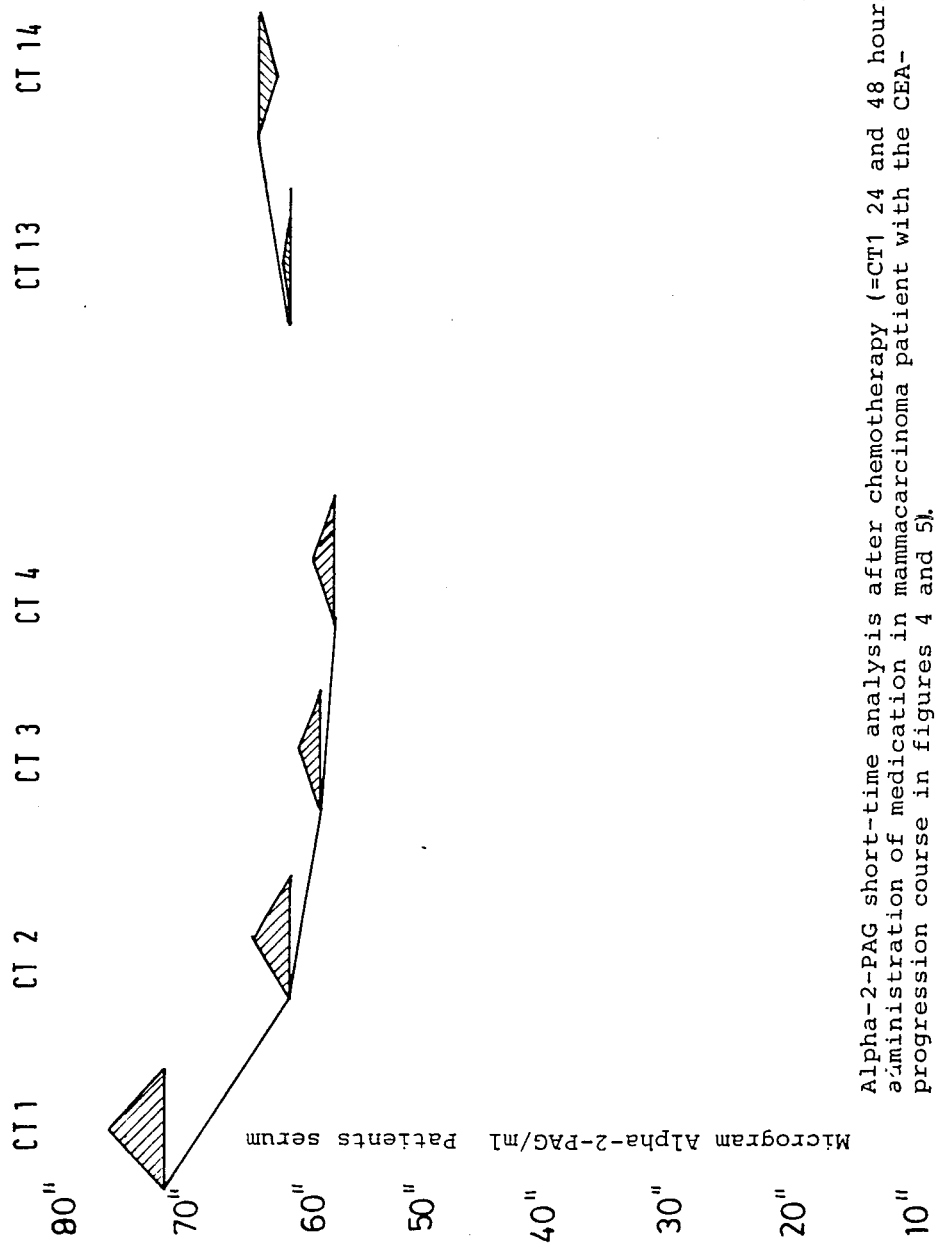

FIGS. 4, 5 and 6

Show the CEA-progression curve of a patient (Mrs. H. G., 53 years, archive No.: M-37) with metastasing mammacarcinoma. CEA (Carcinoembryonic antigen) is a tumor-marker recognized even in medicine-school. The CEA-progression curve gives a picture of the disease progression (FIGS. 4 and 5). Considerable partial remission with chemotherapy (adriblastin monotherapy, 50 mg i.v. (CT 1 to 7) in combination with the radiation of the breast body 3 to 5. After non-effectiveness of hormone methods: tamoxifen and medroxy-progesteronacetate (MPA). At the point of chemotherapy 4: vincristin and mytomycin-C-combination, occurence of a leucopaenia with a massive progression which was contained again with individual dosis of adriblastin. In further progress application of vindesine (vind.) in single doses and then additional doses of adriblastin. Development of a beginning of chemotherapy resistance. Further progression, resistance to therapy and increase of the serum-CEA-level over 600 nanogram/ml.

FIG. 6

Shows the long-time progression from the beginning of a cycle to the beginning of a cycle and the short-time analysis based on the alpha-2-PAG serum level. The contrasting with the CEA-serum levels makes clear the importance of the short-time analysis as a method for predicting the effectiveness/uneffectiveness of a cytostatic therapy.

The invention is not limited to the process hereinbefore described which may be varied in detail.

We claim:

1. A process for the determination of the in vivo effectiveness of a cytostatic agent against immunological active tumors comprising the steps of
   (a) assaying for a marker, an immune parameter, or a mixture thereof in a sample of a serum of a patient having an immunologically active tumor, said marker, parameter, or mixture thereof being produced by the patient, not by the tumor, in response to the tumor,
   (b) administering a cytostatic agent to said patient,
   (c) assaying thereafter for up to 3 days said marker, immune parameter or mixture thereof in further samples of the serum of the same patient, and
   (d) comparing the results of the measurements of steps (a) and (c) to determine the in-vivo effectiveness of the cytostatic agent administered in step (b), wherein an increase in the marker, immune parameter or mixture thereof in step (c) indicates therapeutic effectiveness of the cytostatic agent.

2. The process of claim 1 wherein said marker is alpha-2-PAG.

3. The process of claim 1 wherein said immune parameter is the deviation of complement binding activity.

4. The process of claim 1 wherein said immune parameter is the amount of circulating immune complexes.

5. The process of claim 1 wherein the tumor-specific fractions of said marker, said immune parameter, or mixture thereof are measured only.

6. The process of claim 2 wherein the tumor-specific fractions of said marker, said immune parameter, or mixture thereof are measured only.

7. The process of claim 3 wherein the tumor-specific fractions of said marker, said immune parameter, or mixture thereof are measured only.

8. The process of claim 4 wherein the tumor-specific fractions of said marker, said immune parameter, or mixture thereof are measured only.

* * * * *